(12) United States Patent
Ghadimi et al.

(10) Patent No.: US 12,708,730 B2
(45) Date of Patent: Aug. 18, 2026

(54) FACE MASKS WITH INTERNAL NASAL PRONGS AND METHODS RELATING THERETO

(71) Applicants: Kamrouz Ghadimi, Raleigh, NC (US); Jhaymie Lawrence Cappiello, Raleigh, NC (US)

(72) Inventors: Kamrouz Ghadimi, Raleigh, NC (US); Jhaymie Lawrence Cappiello, Raleigh, NC (US)

( * ) Notice: Subject to any disclaimer, the term of this patent is extended or adjusted under 35 U.S.C. 154(b) by 594 days.

(21) Appl. No.: 18/270,837

(22) PCT Filed: Jan. 3, 2022

(86) PCT No.: PCT/US2022/011006
§ 371 (c)(1),
(2) Date: Jul. 4, 2023

(87) PCT Pub. No.: WO2022/147488
PCT Pub. Date: Jul. 7, 2022

(65) Prior Publication Data

US 2024/0066250 A1 Feb. 29, 2024

Related U.S. Application Data

(60) Provisional application No. 63/133,561, filed on Jan. 4, 2021.

(51) Int. Cl.
*A61M 16/06* (2006.01)
*A61M 16/10* (2006.01)

(52) U.S. Cl.
CPC .... *A61M 16/0672* (2014.02); *A61M 16/0622* (2014.02); *A61M 16/0683* (2013.01); *A61M 16/1065* (2014.02)

(58) Field of Classification Search
CPC .......... A61M 16/0666; A61M 16/0672; A61M 16/0683
See application file for complete search history.

(56) References Cited

U.S. PATENT DOCUMENTS 2,663,297 A * 12/1953 Turnberg .......... A61M 16/0666 D27/135
4,422,456 A * 12/1983 Tiep .................. A61M 16/0666 128/207.18

(Continued)

FOREIGN PATENT DOCUMENTS

GB 2385533 B 8/2005

OTHER PUBLICATIONS

International Search Report and Written Opinion mailed on Mar. 21, 2022 for International Patent Application No. PCT/US2022/011006, pp. 10.

*Primary Examiner* — Kathryn E Ditmer

(57) ABSTRACT

Systems and methods relating to a face mask are described. An exemplar face mask includes: (i) a mask body including an interior side and an exterior side; (ii) inlet ports defined on the mask body; (iii) tubes designed to convey air flow or oxygen flow; (iv) tube transition features coupled to the tubes; (v) nasal prongs coupled to one of the tube transition features and designed to advance the air flow or the oxygen flow into nostrils; (vi) terminating features disposed around and for stabilizing the nasal prongs; and (vii) wherein either the tubes pass through the inlet ports such that portions of the tubes are present on the interior side or the tube transition features pass through the inlet ports such that portions of the tube transition features are present on the exterior side. An exhaust port and an exhaust tube remove exhaled air present inside the mask body.

13 Claims, 6 Drawing Sheets

(56) References Cited

U.S. PATENT DOCUMENTS 4,944,310 A * 7/1990 Sullivan ............ A61M 16/0683 128/207.18
5,438,979 A * 8/1995 Johnson, Jr. ...... A61M 16/0666 128/207.18
7,255,107 B1 * 8/2007 Gomez ............. A61M 16/0666 128/207.18
8,701,669 B2 * 4/2014 Jackman ........... A61M 16/0672 128/207.18
8,915,250 B2 12/2014 Dugan et al.
9,032,955 B2 * 5/2015 Lubke ............... A61M 16/0605 128/206.21
9,333,315 B2 * 5/2016 McAuley ............ A61M 16/024
10,117,599 B2 11/2018 Orr et al.
11,253,670 B1 * 2/2022 Parazynski ....... A61M 16/1005
2002/0053347 A1 * 5/2002 Ziaee .................... A61M 16/06 128/207.18
2005/0011524 A1 * 1/2005 Thomlinson ...... A61M 16/0825 128/207.18
2005/0066976 A1 * 3/2005 Wondka ............ A61M 16/0605 128/207.18
2007/0106382 A1 * 5/2007 Tohara ................... A62B 23/06 623/10
2011/0203591 A1 * 8/2011 Amarasinghe ........ A61M 16/06 128/205.25
2012/0125338 A1 * 5/2012 Yarahmadi ............ A61M 16/12 128/205.25
2012/0167892 A1 * 7/2012 Matula, Jr. ............ A61M 16/06 128/206.21
2012/0305001 A1 * 12/2012 Tatkov .............. A61M 16/0633 128/205.25
2014/0000626 A1 * 1/2014 O'Connor ......... A61M 16/0683 128/207.18
2014/0107517 A1 * 4/2014 Hussain ............ A61M 16/0672 600/114
2014/0166021 A9 * 6/2014 Genger ............. A61M 16/0666 128/207.18
2016/0030695 A1 * 2/2016 Chang ................... A61M 16/06 128/205.25
2017/0246414 A1 * 8/2017 Bahammam ...... A61M 16/0672
2018/0207386 A1 * 7/2018 Kertser ............... A61M 16/085
2019/0076613 A1 3/2019 Amarasinghe
2019/0351170 A1 * 11/2019 Zhan ................. A61M 16/0666
2020/0164170 A1 * 5/2020 Huttner ............... A61M 16/209
2020/0268995 A1 8/2020 Shin
2021/0016050 A1 * 1/2021 Zoellner ............... A61M 16/06

* cited by examiner

FACE MASKS WITH INTERNAL NASAL PRONGS AND METHODS RELATING THERETO

RELATED APPLICATION

This application is a National Stage Application of International Application No. PCT/US22/11006 filed on Jan. 3, 2022 which further claims priority from US Patent Application having Ser. No. 63/133,561 respectively filed on Jan. 4, 2021, which is incorporated herein by reference for all purpose.

FIELD

The present arrangements and teachings relate generally to novel face masks and methods for assembling and using thereof. More particularly, the present arrangements and teachings relate to novel face masks design and for methods relating thereto that are particularly adapted to efficiently and effectively deliver high-flow fresh gas, air and/or oxygen to a subject who may be requiring respiratory assistance or suffering from an infection that has caused a pandemic, such as an infection caused by the SARS-CoV-2 ("COVID-19") or influenza ("Flu") viruses.

BACKGROUND

Patients suffering from respiratory infections, including COVID-19, frequently complain of shortness of breath. People with chronic heart, lung, and blood diseases may be at risk of severe respiratory symptoms, including pneumonia, acute respiratory distress, and acute respiratory failure. In these or similar instances, for example, it is important to administer high-flow oxygen to these patients to save their lives. Unfortunately, the current non-invasive oxygen delivery systems and methods are therapies that merely bridge patients to more invasive methods of oxygenation. This is because these devices are not effective as definitive treatment and fail to efficiently deliver the requisite high flow rates of oxygen to patients without losing a considerable proportion of the oxygen and air delivery to the environment. Definitive treatment for accomplishing high flow rates of oxygen include performing a tracheal intubation and subjecting the patient to invasive mechanical ventilation, which gravely impact clinical outcomes of these severely ill patients who have entrusted their livelihood to the healthcare system. Moreover, frequently during the current non-invasive high flow oxygen-delivery process, healthcare workers are exposed to harmful aerosols, e.g., aerosolized viral particles that are generated from the patient's nasopharyngeal cavity from the high flow that interfaces with nasopharyngeal mucosa; this mucosal surface is known to harbor viral particles that induce infectious transmissibility. With supply chain concerns limiting steady flow of personal protective equipment for healthcare workers, a patient-centered solution could limit healthcare worker exposure to airborne respiratory infection by providing an added layer of protection.

Thus, there is a critical need to effectively and safely administer high-flow oxygen to patients without suffering from the drawbacks encountered by the current oxygen delivery systems and methods.

SUMMARY

The present arrangements and teachings offer systems and methods relating thereto for effectively and safely administering high-flow oxygen to patients with desirable clinical outcomes and without posing a risk of infection to the health care workers.

In one aspect, the present arrangements offer novel mask designs. One such exemplar face mask includes: (i) a mask body including an interior side and an exterior side, wherein the interior side is designed to cover a mouth and a nose of a subject and encloses conditions inside the mask body, and wherein the exterior side is typically exposed to ambient conditions or conditions outside the mask body; (ii) at least two inlet ports defined on the mask body and designed to provide access between the exterior side and the interior side of the mask body; (iii) at least two tubes designed to convey air flow or oxygen flow and at least a portion of each of the tubes is disposed on the exterior side of the mask body; (iv) at least two tube transition features, each of which is communicatively coupled to one of the tubes and including a portion that is disposed on the interior side of the mask body and is designed to advance the air flow or the oxygen flow from the tube communicatively coupled to the tube transition feature; (v) at least two nasal prongs, each of which is communicatively coupled to one of the tube transition features and designed to receive the air flow or the oxygen flow from the tube transition feature and designed to further advance the air flow or the oxygen flow towards or into the nostrils of the subject; (vi) at least two terminating features, each of which is disposed around the nasal prongs and designed to occupy or stabilize the nasal prongs within nasal cavity defined in the nostril of the subject.

In this configuration, there are alternate arrangements for facilitating air flow or oxygen flow between an exterior side and an interior side of the face mask. In certain embodiments of the present arrangements, at least two of the tubes pass through at least two of the inlet ports such that portions of at least two of the tubes are present on the interior side of the mask body. In certain of the alternate embodiments, at least two of the tube transition features pass through at least two of the inlet ports such that portions of at least two of the tube transition features are present on the exterior side of the mask body.

Regardless of whether the tubes or tube transition features pass through the inlet ports, the face mask, preferably, further includes an exhaust port disposed on the mask body at a region that is designed to be near the mouth of the subject. The exhaust port is designed to remove, out of the mask body, the subject's exhaled air present inside the interior side.

The present face mask design preferably further includes a single source tube extending to at least one Y-split that is designed for splitting the air flow and/or the oxygen flow inside the single source tube into at least two of the tubes. In this arrangement, the single source tube is communicatively coupled (e.g., either directly or indirectly connected) to a source of the air flow and/or the oxygen flow. In certain embodiments of the present arrangements, the single source tube and/or at least two of the tubes include smooth-bore tubing to facilitate high-flow oxygen and/or high-flow air delivery. In these embodiments, the face mask may further include: (i) a circumferential clip disposed around each of the tubes; and (ii) an adjustable head strap that couples, at one end, to the circumferential clip end and is designed, at another end, to be disposed behind a head of the subject and thereby stabilizing positioning of at least two of the tubes. The single source tube and/or at least two of the tubes may be made from a corrugated material for facilitating efficient air flow and/or oxygen flow.

The present face mask preferably further includes a peripheral seal disposed around a periphery of the mask body. In this configuration, the peripheral seal may include a gel or an inflatable portion designed for snugly fitting the mask body around at least the mouth and the nose of the subject.

The terminating feature of the face mask preferably has a tapered shape. In certain embodiments of the present arrangements, the terminating feature includes a first umbrella seal and a second umbrella seal. The first umbrella seal may include a first base portion having a first diameter or a first dimension (e.g., a length or a width of one side of the first base portion). The second umbrella seal may, similarly, include a second base portion having a second diameter or a second dimension corresponding to the first dimension. In this arrangement, the first base portion is closer in distance than the second base portion to the tube transition feature that is communicatively coupled to the terminating feature. Further, in this arrangement, the first base portion has a greater diameter than the second base portion or the first dimension is larger than the corresponding second dimension (e.g., a corresponding length or a corresponding width of one side of the second base portion).

The face mask may further include a bridge feature having defined therein at least two inlet apertures designed for receiving the air flow and/or the oxygen flow from at least two of the tubes. Further, the bridge feature structurally integrates at least two of the tube transition features such that, during an operative state of the bridge feature, the air flow and/or the oxygen flow received from at least two of the tubes is advanced to at least two of the tube transition features.

When at least two of the tubes pass through at least two of the inlet ports such that the portions of at least two of the tubes is present on the interior side of the mask body, then at least two of the tubes are arranged to angularly displace about respective ones of at least two of the inlet ports. In this present arrangement, angular displacement of at least two of the tubes facilitates adjustment of the terminating ends (which are communicatively coupled to the tubes) inside the subject's nostrils.

When at least two of the tube transition features pass through at least two of the inlet ports such that portions of at least two of the tube transition features is present on the exterior side of the mask body, then at least two of the tube transition features are arranged to angularly displace about respective ones of at least two of the inlet ports. In this present arrangement, angular displacement of at least two of the tube transition features facilitates adjustment of the terminating ends (which are communicatively coupled to the tube transition features) inside the subject's nostrils.

In certain embodiments of the present arrangements, at least a front portion of the mask body is transparent to allow visibility into the interior side of the mask body and into the position of at least two of the nasal prongs for facilitating adjustment into the nostril of the subject.

The face mask preferably further includes one or more secondary airflow ports designed to house an embedded filtration element. In one embodiment of the present arrangements, the embedded filtration element filters out at least 95% of the air borne particles.

In certain configurations, the present face mask further includes a high-efficiency particulate air ("HEPA") filter coupled to an exhaust tube, which is connected to the exhaust port. The present teachings recognize that the presence of one or more secondary airflow ports limit pressure build up within the mask body to allow steady inflow of fresh gas, e.g., air flow and/or oxygen flow, and steady outflow of exhaled gas and aerosol via a scavenge/exhaust port.

The present face mask may further include one or more mounting features of securing thereon retention straps being designed to secure the mask body around the mouth, the nose and, preferably, a chin of the subject.

In another aspect, the present teachings offer methods for securing a face mask around a subject. One such exemplar method includes obtaining a mask body having disposed therein at least two nasal prongs, each of which terminates at a terminating end. Next, the exemplar method includes positioning at least two of the terminating ends inside nostrils of a subject so that the terminating end is positioned to effectively supply air flow and/or oxygen flow into the nostrils of the subject. Then the exemplar method proceeds to a step, which includes wrapping one or more retention straps, which are attached to or part of the mask body, around a head of the subject and securing the mask body to the head of the subject such that the terminating end continue to effectively provide air flow and/or oxygen flow into the nostrils of the subject.

The above-described exemplar method for securing preferably further includes receiving the air flow and/or the oxygen flow into at least two of the terminating ends from at least two tube transition features, which are communicatively coupled to at least two tubes, which are in turn communicatively coupled through a Y-split to a single tube, which in turn is communicatively coupled to an air supply source and/or an oxygen supply source. In this configuration, to avoid unobstructed flow of air and/or oxygen, the exemplar method may further include ensuring placement of the Y-split behind a head of the subject. The above-mentioned method for securing may further include either inflating a peripheral seal and/or applying a gel to the peripheral seal, which is disposed around a circumference of the mask body. Such steps ensure that the mask body snugly fits around a mouth, a nose, and, preferably, a chin of the subject, without cause damage to the subject's face particularly in instances of prolonged use of the face mask.

In yet another aspect, the present teachings provide many different methods for assembling a face mask. One such exemplar method begins with obtaining a mask body having defined therein, on or near a mask body region that covers nostrils of a subject, at least two inlet ports that provide access between an exterior side of the mask and an interior side of the mask. The beginning of the exemplar method, preferably, includes obtaining at least two tubes that are, or subsequently may be, communicatively coupled to a source of air and/or a source of oxygen. The beginning of the exemplar step may also include obtaining at least two tube transition features that are integrated with or coupled to at least two nasal prongs.

The exemplar methods for assembling the face mask of the present arrangements then, preferably, proceeds to passing, from the exterior side to the interior side, at least two of the tubes through at least two of the inlet ports. Alternately, in another embodiment of the present teachings, the exemplar method includes passing, from the interior side to the exterior side, at least two of the tube transition features, and not passing the tubes, through at least two of the inlet ports. Regardless of whether the tubes or the tube transition features pass through the inlet ports, the exemplar method includes coupling at least two of the tube transitioning features to at least two of the tubes to assemble the face mask of the present arrangements.

Exemplar methods for assembling preferably include obtaining a mask body that also has defined therein an exhaust port. In these embodiments of the present teachings, the exemplar methods include communicatively coupling an exhaust tube to the exhaust port disposed on the mask body. The exhaust tube is, more preferably, coupled to a high-efficiency particulate air ("HEPA") filter for filtering out harmful toxins from the subject's expelled exhaled air.

In other preferred implementations of this exemplar method for assembling, the step of obtaining at least two tube transition features includes using a bridge feature. The bridge feature structurally integrates at least two inlets and at least two of the tube transition features. The preferred implementations may then proceed to coupling at least two of the tubes with at least two of the inlets or coupling at least two of the tube transition features with at least two of the nasal prongs. It does not matter which coupling step is performed first so long as the tubes, tube transition features (of the bridge feature) and nasal prongs are connected to form at least a portion of the face mask of the present arrangements.

The construction and method of operation of the invention, however, together with additional objects and advantages thereof, will be best understood from the following descriptions of specific embodiments when read in connection with the accompanying figures.

BRIEF DESCRIPTION

DETAILED DESCRIPTION

In the following description numerous specific details are set forth in order to provide a thorough understanding of the present invention. It will be apparent, however, to one skilled in the art that the present invention may be practiced without limitation to some or all of these specific details. In other instances, well known process steps have not been described in detail to not unnecessarily obscure the invention.

Figure 1:
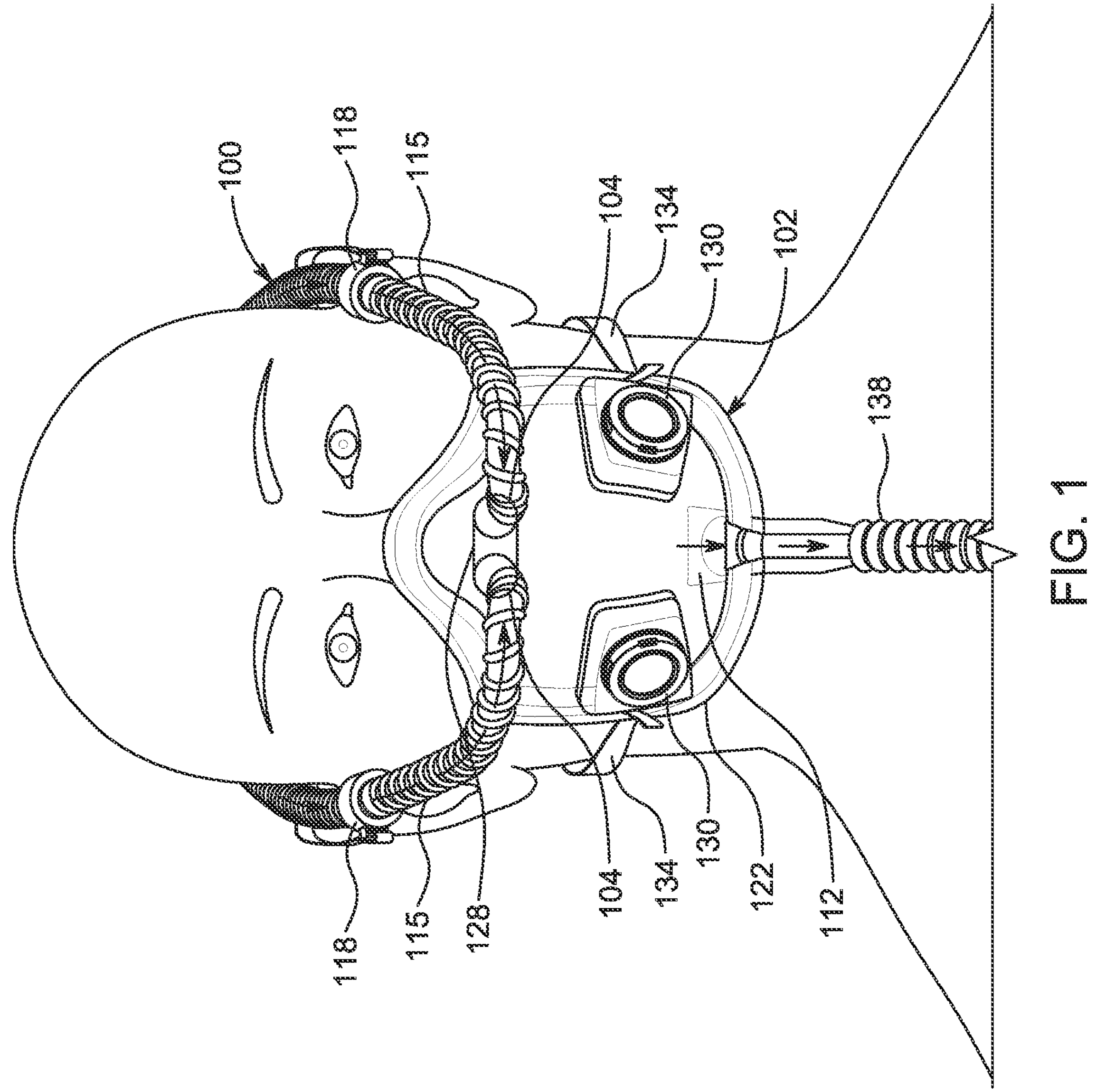
FIG. 1 shows a front, perspective view of a face mask, according to one embodiment of the present arrangements, fitted on a subject and including tubes facilitating air flow and/or oxygen flow from an exterior side to an interior side of the face mask.

FIG. 1 shows a face mask 100, according to one embodiment of the present arrangements, including a mask body 102, which has defined therein at least two inlet ports 104 that provide access between an exterior side and an interior side of mask body 102. In this arrangement, at least two tubes 115 pass through inlet ports 104 and serves as a conveyance for air flow and/or oxygen flow from the exterior side to the interior side of mask body 102. The exterior side is typically exposed to ambient conditions or conditions outside mask body 102. The interior side of mask body 102 is designed to cover a subject's mouth, nose and, preferably, chin and enclose the conditions present inside mask body 102. As a result, a healthcare worker, for example, is protected from the harmful aerosolized viral particles generated from a patient's nasopharyngeal cavity and expelled from the patient's mouth during a bout with the COVID-19 virus. In the interior side of mask body 102, inlet ports 104 are designed to provide access to a subject's nostrils.

Mask body 102 includes an exhaust port 112, a peripheral seal 122 and one or more secondary airflow ports 130. Exhaust port 112 is disposed around a mask body region that covers the subject's mouth so that the subject's exhaled air present inside the interior side of mask body 102 is expelled out through an exhaust tube 138, as shown in FIG. 1.

Peripheral seal 122 serves to seal off the interior side of mask body 102 against a patient's face. Accordingly, peripheral seal 122 seals off the harmful contents, posing a threat to other individuals, such as healthcare workers, trapped inside mask body 102 from escaping to the exterior of mask body 102. In certain embodiments of the present arrangements, peripheral seal 122 includes a soft gel material that facilitates in the formation an effective seal that does not hurt the patient when the face mask is applied to a patient particularly for long periods of time. As explained below in connection with FIGS. 4 and 5, peripheral seal 122, alternately, may be an inflatable portion disposed around a periphery of mask body 102 and designed for snugly fitting mask body around the mouth, nose, and, preferably, chin of the subject.

In FIG. 1, secondary airflow ports 130 are designed to house an embedded filtration element. By way of example, an N95 mask, which filters out at least 95% of the air borne particles, may be disposed inside each of secondary airflow ports 130.

In connection with the provisions of delivery of air flow and/or oxygen flow, FIG. 1 shows at least two tube transition features 106 that are communicatively coupled, at a receiving end, to at least two of tubes 115 and are connected, at a terminating end, to at least two terminating features 110. The term "communicatively coupled," as used in this specification, conveys both "direct" or "indirect" connections. By way of example, as explained in reference to FIG. 2, tubes 115 are "communicatively coupled" to tube transition features 106 because the two components are indirectly connected. Specifically, in the embodiment of FIG. 2, the presence of a bridge feature 128, an intermediate feature or component, facilitates the connection between tubes 115 and tube transition features 106.

It is noteworthy that bridge feature 128 is an optional feature in the present arrangements and that, in the absence of bridge feature 128, tubes 115 may be directly connected, i.e., also "communicatively coupled," to tube transition features 106. By way of example, in the arrangement of FIG. 1, each of two tube transition features 106 is communicatively coupled (e.g., directly connected) to one of tubes 115.

In the present arrangements of different face mask designs, tube transition feature 106 in its entirety (e.g., tube transition features 106 shown in FIGS. 1 and 2), or at least a portion of tube transition feature (e.g., tube transition features 106' shown in FIG. 3), is disposed on the interior side of mask body 102. Regardless of how much of tube transition feature 106 is present on the interior side, each of the tube transition features 106 advance air flow and/or oxygen flow received from their respective tubes 115 or their communicatively coupled ones of tubes 115, i.e., a particular tube 115 that is communicatively coupled to tube transition feature 106.

On the other end of tube transition features 106, at least two nasal prongs 108 (e.g., shown in FIG. 2) are provided in face mask 100. Each of nasal prongs 108 is communicatively coupled to one of tube transition features 106 and designed to receive air flow and/or oxygen flow from at least one of tube transition feature 106. In this configuration, nasal prong 108 further advances the air flow and/or the oxygen flow, received from its respective tube transition feature 106, i.e., the communicatively coupled ones of tube transition features 106, towards the nostrils of a subject, e.g., a patient.

Figure 2:
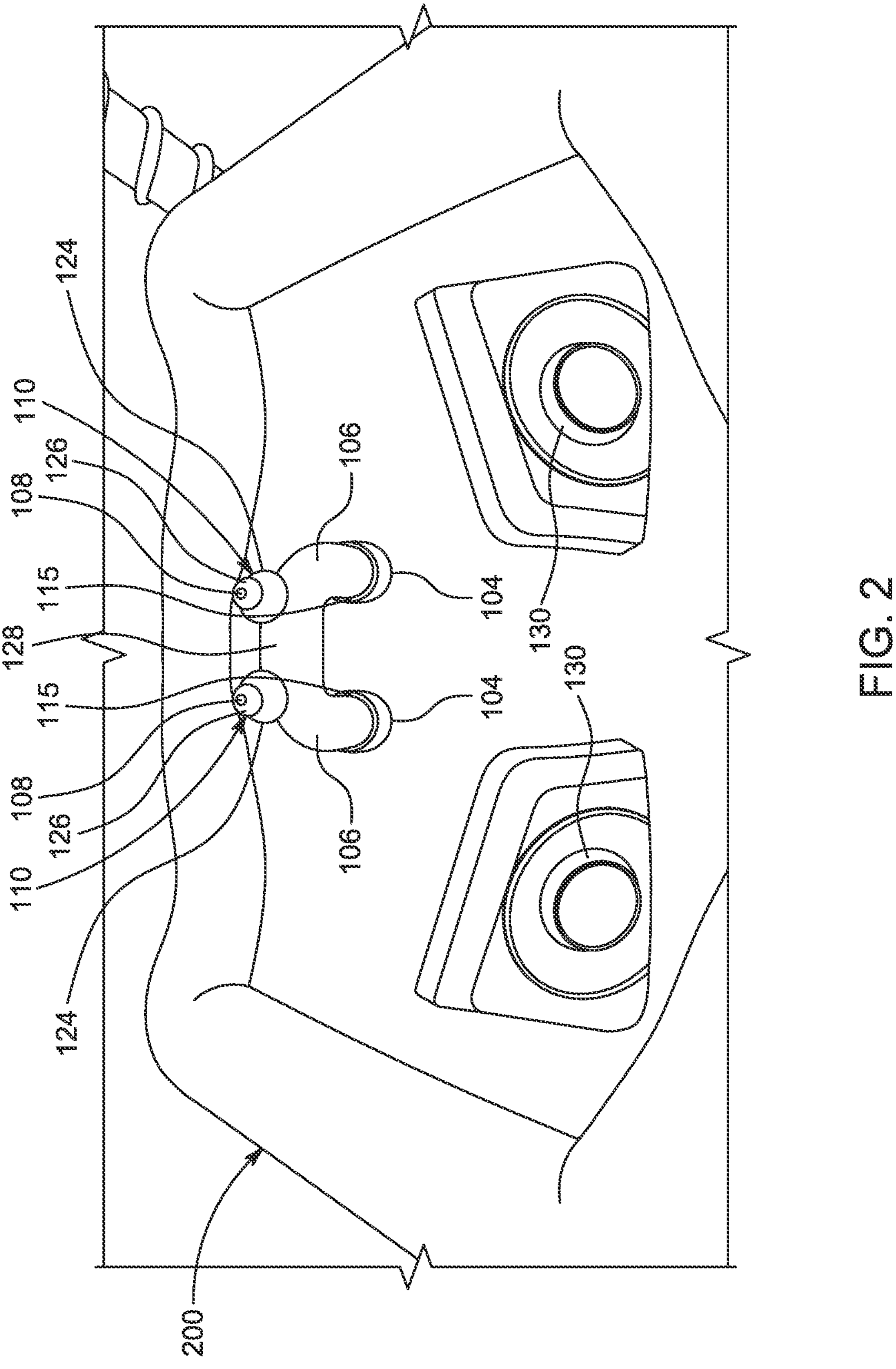
FIG. 2 shows a front view of an interior side of the face mask of FIG. 1 including tubes that extend and deliver air and/or oxygen flow from an exterior side to an interior side of the face mask.

At least two nasal prongs 108 are communicatively coupled to terminating features (e.g., terminating features 110 shown in FIG. 2). In an operative state of face mask 100, terminating features 110 occupy, or stabilize nasal prongs (e.g., nasal prongs 108 shown in FIG. 2) within the nasal cavity, inside the subject's nostrils. In this configuration, nasal prongs 108 operate in conjunction with terminating features 110 to effectively and efficiently provide air flow and/or oxygen flow directly into the subject's nostrils.

In face mask 100 of FIG. 1, tubes 115, tube transition features 106 (shown in FIG. 2), and nasal prongs 108 (shown in FIG. 2) may be implemented as a single unitary structure obtained through, for example, an extrusion process. Alternately, each or some of these are features or separate components that are assembled by serial connection, e.g., tubes 115 are connected to tube transition features 106, which are in turn connected to nasal prongs 108, or assembled by connecting a component to a partial integration of components incorporating certain features obtained by extrusion. In any of these different approaches of producing face mask 100, terminating ends 100 may be fitted on to or may represent an integrated feature of nasal prongs 108. The present teachings recognize that fabrication processes such as injection molding may be used to produce features, components or unitary structures of certain integrated components and/or features. Regardless of the approach adopted, in some of these embodiments of the present arrangements, a bridge feature (denoted by reference numeral 128 in FIG. 2) is optional and not a necessary element of the present arrangements.

Turning to certain fastening features of face mask 100, FIG. 1 shows a circumferential clip 118 disposed around each of tubes 115. Further, an adjustable head strap (e.g., a head strap 120 shown in FIG. 4) couples, at one end, to circumferential clip 118 and, at another end, is secured and disposed behind a patient's head. In this operational state of adjustable head strap 120, tube 115 are properly positioned, secured and stabilized around the subject's head to allow for unobstructed air flow and/or oxygen flow to the subject's nostrils.

In preferred implementations of present face mask 100, tubes 115 when secured, according to present teachings and using adjustable head strap 120, do not come in the subject's direct line of sight, e.g., tubes 115 are not positioned over mask body 102, to avoid engendering overwhelming feelings of a respiratory malady. In such preferred implementations, tubes 115 are positioned discretely to sides of mask body 102 such that the presence of tubes 115 may be visible, if at all, to the subject through their peripheral vision.

FIG. 1 shows that at least two of tubes 115 pass through at least two of inlet ports 104 such that portions of at least two tubes 115 is present on said interior side of mask body 102. Preferably, a small portion of tubes 115, in the order of a few millimeters and, preferably, a length of tube 115 ranging from about 1 mm to about 10 mm, and, more preferably ranging from about 1 mm to about 5 mm, is present on interior side of mask body 102.

FIG. 2 shows a face mask 200, according to another embodiment of the present arrangements and in greater detail an interior side of mask body 102, which is the same as that shown in FIG. 1. According to FIG. 2, face mask 200 includes portions of at least two tubes 115 primarily disposed at an exterior side (as shown in FIG. 1), passing through at least two inlet ports 104 (as shown in FIG. 2) and extending into the interior side of mask body 102 (see a small portion of tube 115 extending into the interior side shown in FIG. 2). Inlet ports 104, tubes 115 and secondary airflow ports 130 of face mask as shown in FIG. 2 are the same as the features of face mask 100 shown in FIG. 1. FIG. 2 shows nasal prongs 108 having disposed therein terminating features 110.

Each terminating feature 110 has disposed thereon a first umbrella seal 124 and an adjacent second umbrella seal 126. First umbrella seal 124 includes a first base portion having a first diameter, if first umbrella seal 124 is circular in shape, or a first dimension, such as a dimension of a side, if first umbrella seal 124 is polygonal-shaped. Similarly, second umbrella seal 126 includes a second base portion having a second diameter, if second umbrella seal 126 is circular in shape, or a second dimension, such as a dimension of a side, if second umbrella seal 126 is polygonal-shaped. In cases of polygonal-shaped first umbrella seal 124 and second umbrella seal 126, the second dimension of second umbrella seal 126 is, preferably, smaller than a corresponding first dimension of first umbrella seal 124. If first umbrella seal 124 and second umbrella seal 126 are circular, and not polygonal-shaped, however, then the first diameter is, preferably, larger than the second diameter. As a result, first umbrella seal 124 and, an adjacently disposed, second umbrella seal 126, are arranged to create a "tapered" structure of terminating feature 110. As shown in FIG. 2, the first base portion (of first umbrella seal 124) is closer in distance than the second base portion (of second umbrella seal 126) to a reference point, e.g., a tube transition feature that is communicatively coupled to the particular terminating feature 110.

Face mask 200, as shown in FIG. 2, comprises an optional bridge feature 128 including at least two inlets for receiving at least two tubes 115 and including at least two tube transition features 106 that couple to or are integrated with at least two nasal prongs 108. In other words, bridge feature 128 communicatively couples at least two tubes 115 and at least two nasal prongs 108 through or by virtue of at least two tube transition features 106 disposed therewithin. In this arrangement, bridge feature 128 structurally integrates at least two tube transition features such that, during an operative state of face mask 200, the air flow and/or the oxygen flow received from tubes 115 (shown in FIG. 1) is advanced, through at least two of tube transition features 106, to at least two nasal prongs 108.

Figure 3:
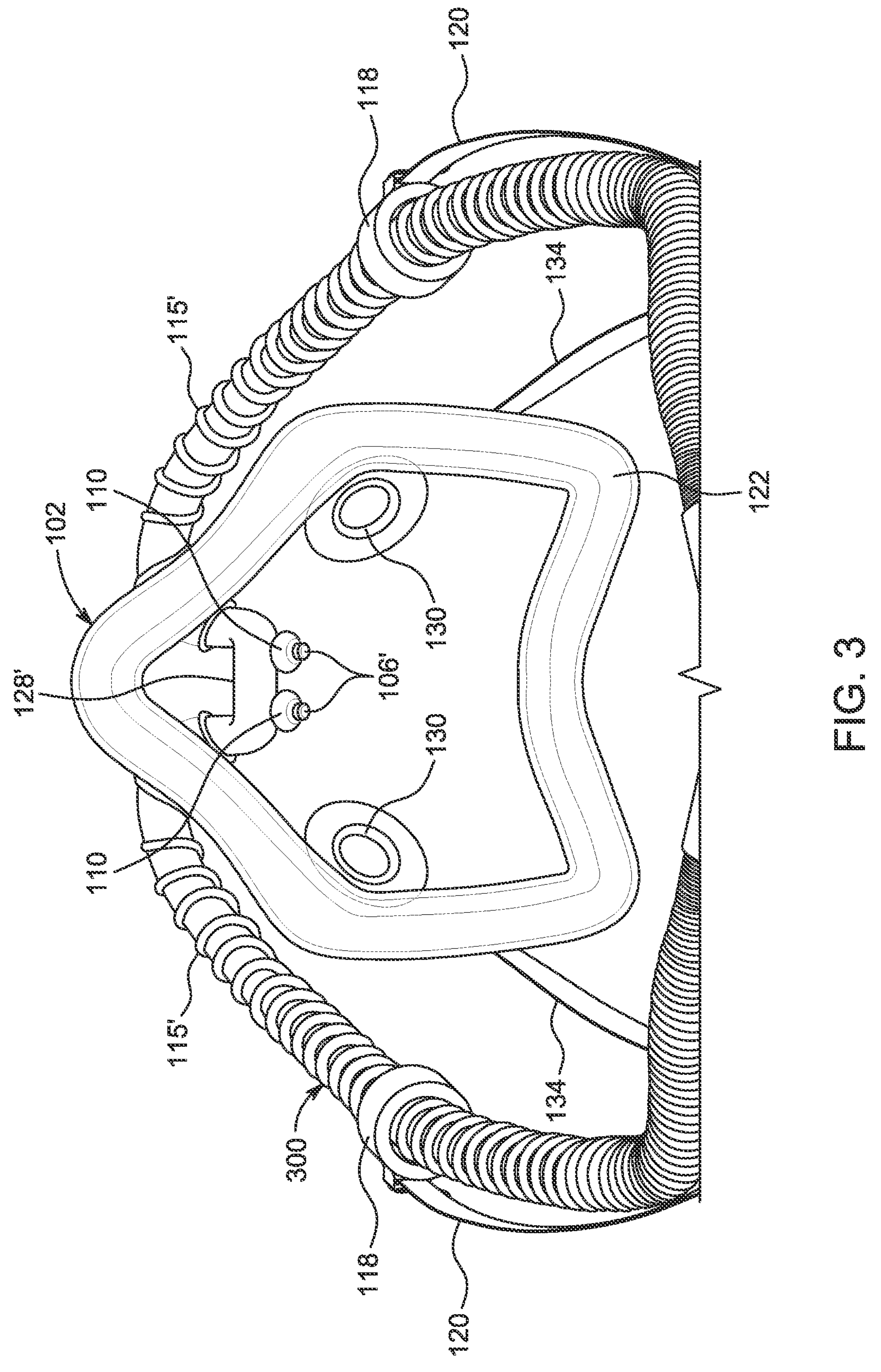
FIG. 3 shows a front view of a portion of the interior side of a face mask, according to another embodiment of the present arrangements, including tube transition features that extend and deliver air and/or oxygen flow from an exterior side to an interior side of the face mask.

The present teachings recognize that tubes 115 do not have to pass through inlet ports 104 to provide air flow and/or oxygen flow inside mask body 102. In certain embodiments of the present arrangements, tube transition features 106 pass through inlet ports 104 and extend to the exterior side of mask body 102 to communicatively couple with their respective tubes. To this end, FIG. 3 shows at least two tubes 115', which are disposed on the exterior side of mask body 102 and do not extend into the interior side of mask body 102, communicatively coupled to at least two tube transition features 106'. In this arrangement of face mask 200, at least two tube transition features 106' pass through at least two inlet ports 104 such that portions of at least two tube transition features 106' are present on the exterior side of mask body 102.

It is important to bear in mind that tubes 115, shown in FIGS. 1 and 2, extend from the exterior side to the interior side of mask body 102. In sharp contrast, tubes 115', shown in FIG. 3, do not so extend and are disposed only on the exterior side of mask body 102. Further, tube transition features 106, shown in FIGS. 1 and 2, are disposed only in the interior side of mask body 102, but tube transition features 106', shown in FIG. 3, are not so limited and extend from the interior side to the exterior side of mask body 102. These differences in different embodiments of tubes and/or tube transition features are not intended to limit the scope of present arrangements, rather these different embodiments expand the scope of present arrangements to include implement or integrate these different embodiments of tubes and/or tube transition features for facilitating effective and efficient air flow and/or oxygen flow into a subject's nostrils.

Except for the above-mentioned differences between tubes 115, shown in FIGS. 1 and 2, and tubes 115', shown in FIG. 3, and tube transition features 106, shown in FIGS. 1 and 2, and tube transition features 106', shown in FIG. 3, FIGS. 1, 2 and 3 are similar. By way of example, other components of a face mask 300 shown in FIG. 3, such as mask body 102, terminating features 110, circumferential clip 118, adjustable wrap 120, and peripheral seal 122 are the same as those of face mask 100, shown in FIG. 1, and of face mask 200 shown in FIG. 2. Further, bridge feature 128' of face mask 300, shown in FIG. 3, is the same as that of face mask 200 shown in FIG. 2, except bridge feature 128 in FIG. 2 is disposed in the interior side of mask body 102 and bridge feature 128' in FIG. 3 is disposed in the exterior side of mask body. Face mask 300 shows a retention strap 134 for securing mask body 102 to a patient's head and such a strap may be used in connection with face mask 100 and 200 of FIGS. 1 and 2, respectively. As a result, during an operational state of the face masks, according to the present arrangements, tubes 115 or 115', by virtue of adjustable wrap 120, and mask body 102, by virtue of retention strap 134, are secured to a patient's head.

Although face mask 300 of FIG. 3 includes an exhaust port 112 and exhaust tube 138 as shown in FIG. 1, they are not shown in FIG. 3 to simplify illustration and emphasize the structural details of the components and features involved in conveying air flow and/or oxygen flow into the patient's nostrils.

In an arrangement, in which at least two of tubes 115 shown in FIG. 1 pass through at least two of inlet ports 104 such that portions of at least two of tubes 115 are present on the interior side of mask body 102, each tube 115, preferably, angularly displaces about its respective inlet port 104. Alternately, when each tube transition feature 106', shown in FIG. 3, passes through its respective inlet port 104, each tube transition feature 106' angularly displaces about its respective inlet port 104. According to preferred embodiments of the present arrangements, at least either tubes 115, as shown in FIGS. 1 and 2, or tube transition features 106', as shown in FIG. 3, angularly displace about their respective inlet ports 104 and thereby allow adjustment of nasal prongs 108 (which are communicatively coupled to tubes and tube transition features) inside the subject's nostrils.

Figure 4:
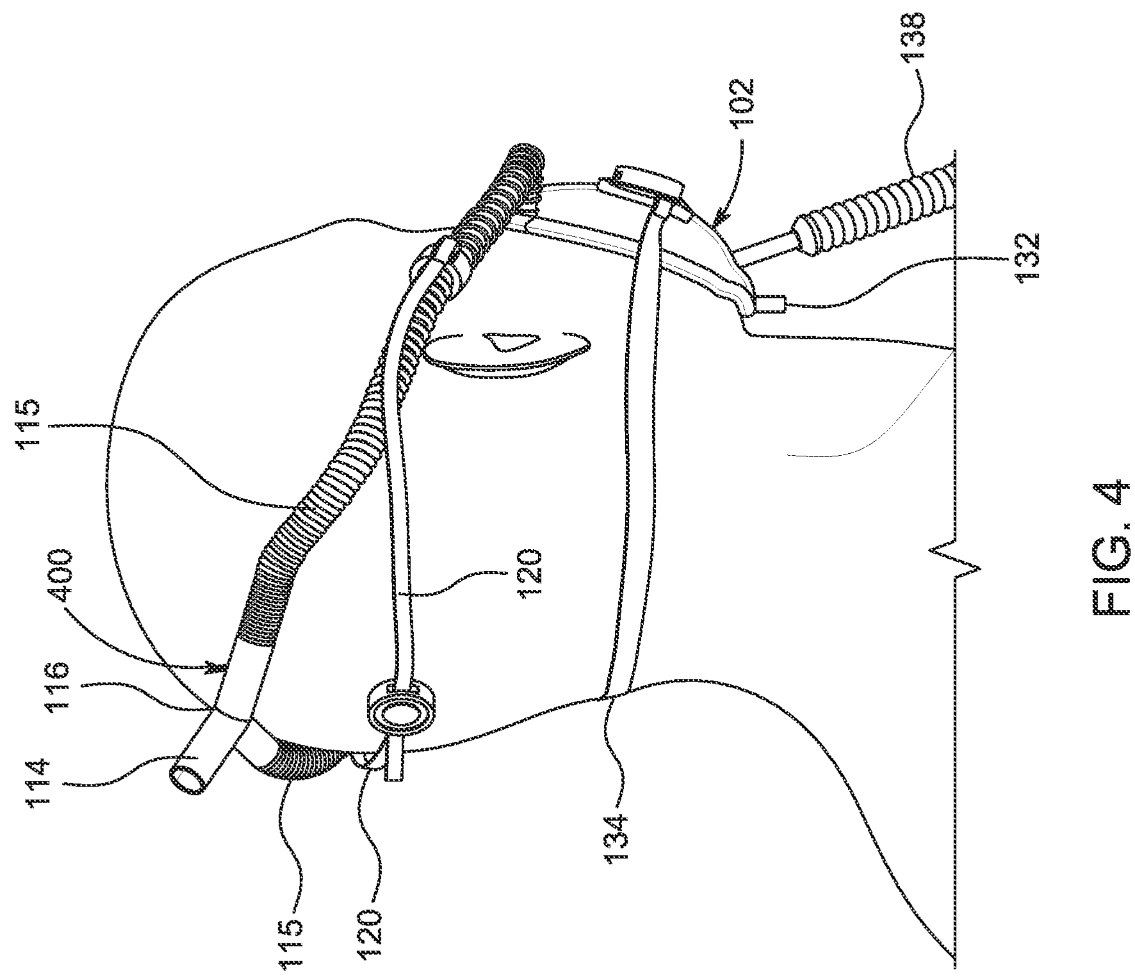
FIG. 4 shows a side view of a face mask, which may be either of FIG. 1 or 3, fitted on a subject and showing different types of components, according to one embodiment of the present arrangements, involved in securing the tubes and the mask body to the subject and involved in providing unobstructed air flow and/or oxygen flow to the subject.

FIG. 4 shows a face mask 400 applied to a subject's (e.g., a patient's) head. According to this figure, a single source tube 114 is communicatively coupled to a source (not shown to simplify illustration) of air flow and/or oxygen flow. Structurally, single source tube 114 extends to at least one Y-split 116 that is designed for splitting the air flow and/or the oxygen flow inside single source tube 114 into at least two tubes (e.g., tubes 115, shown in FIGS. 1 and 2, and tubes 115' shown in FIG. 3). Single source tube 114 and/or at least two said tubes (e.g., single source tubes 115 of FIG. 1 or single source tubes 115' of FIG. 3) are preferably made from a corrugated material for facilitating efficient air or oxygen flow. Further, in more preferred embodiments of the present arrangements, single source tube 114 and/or at least two said tubes (e.g., tubes 115, shown in FIGS. 1 and 2, and tubes 115' shown in FIG. 3) include smooth-bore tubing to facilitate high-flow oxygen and high-flow air delivery.

In FIG. 4, mask body 102, tubes 115, and exhaust tube 138 of face mask 400 are the same as those of face mask 100 shown in FIG. 1. Retention strap 134 and adjustable head strap 120 of face mask 400, shown in FIG. 4, are the same as those of face mask 300 shown in FIG. 3, except adjustable head strap 120 in FIG. 4 is shown to be secured behind a subject's head using, for example, a slidable adjuster that slides to take up a slack of head strap 120 and thereby allows head strap 120 to snugly fit around a subject's head.

Peripheral seal 122 of FIG. 1 may be an inflatable seal. To this end, face mask 400 shown in FIG. 4 includes an inflatable valve 132, which when activated, allows peripheral seal 122 of FIG. 4 to inflate and thereby effectively operate as a seal, i.e., sealing off the environment inside mask body 102, without applying undue pressure on and thereby not hurting the subject's face, particularly during prolonged application of the mask body on the subject's face.

Figure 5:
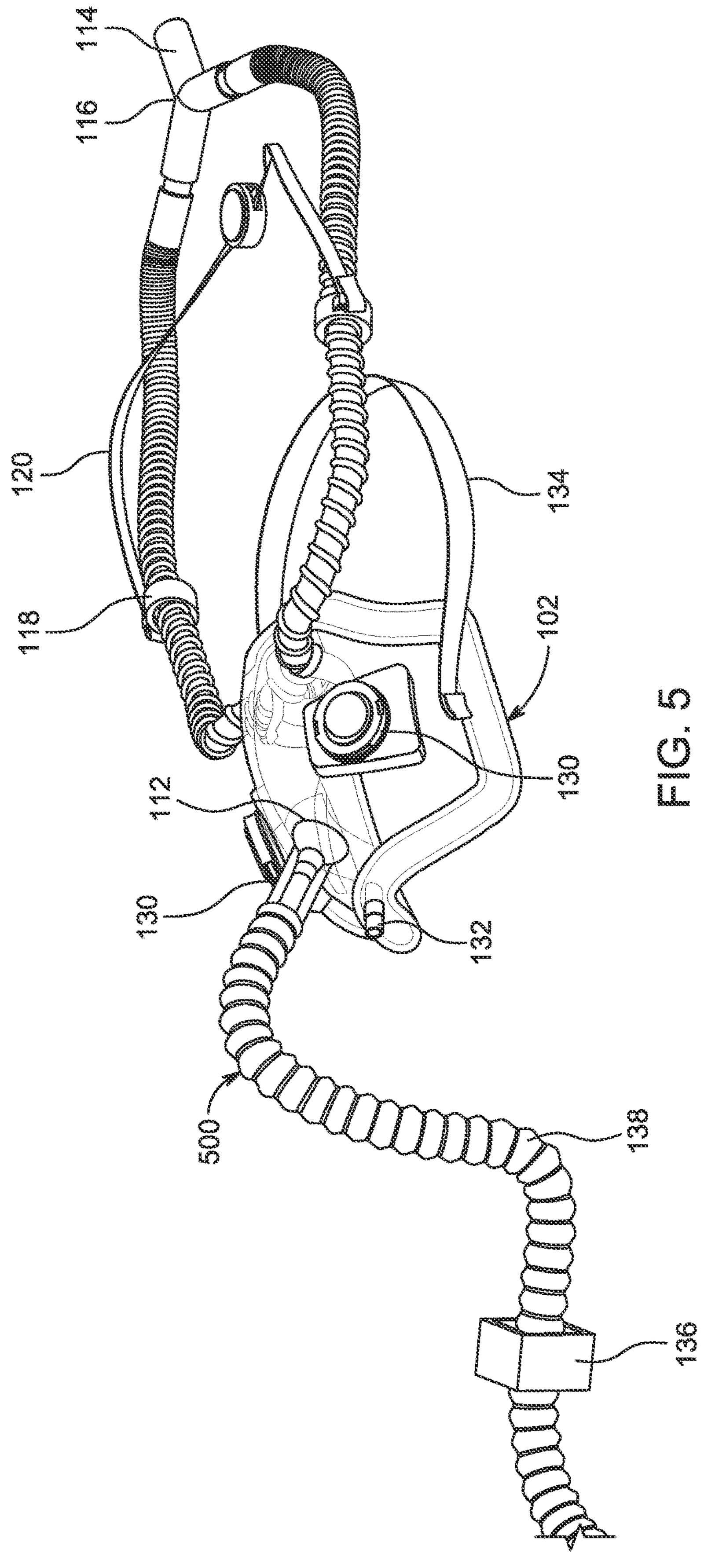
FIG. 5 shows a side view of a face mask, according to another embodiment of the present arrangements, including an inflatable peripheral seal and an inflatable valve.

FIG. 5 shows a face mask 500, according to certain preferred embodiments of the present arrangements, including mask body 102, exhaust port 112, single source tube 114, Y-split 116, circumferential clip 118, adjustable head strap 120, secondary airflow ports 130, inflatable valve 132, retention strap 134 and exhaust tube 138, all of which are the same as discussed above as features and/or components of the face masks shown FIGS. 1-4. Moreover, tubes 115' and tube transition features 106' shown in FIG. 3 are easily implemented in the arrangement shown in FIG. 5. FIG. 5 further shows a high-efficiency particulate air ("HEPA") filter 136 disposed downstream from exhaust tube 138 to filter out harmful toxins from the subject's exhaled air.

Figure 6:
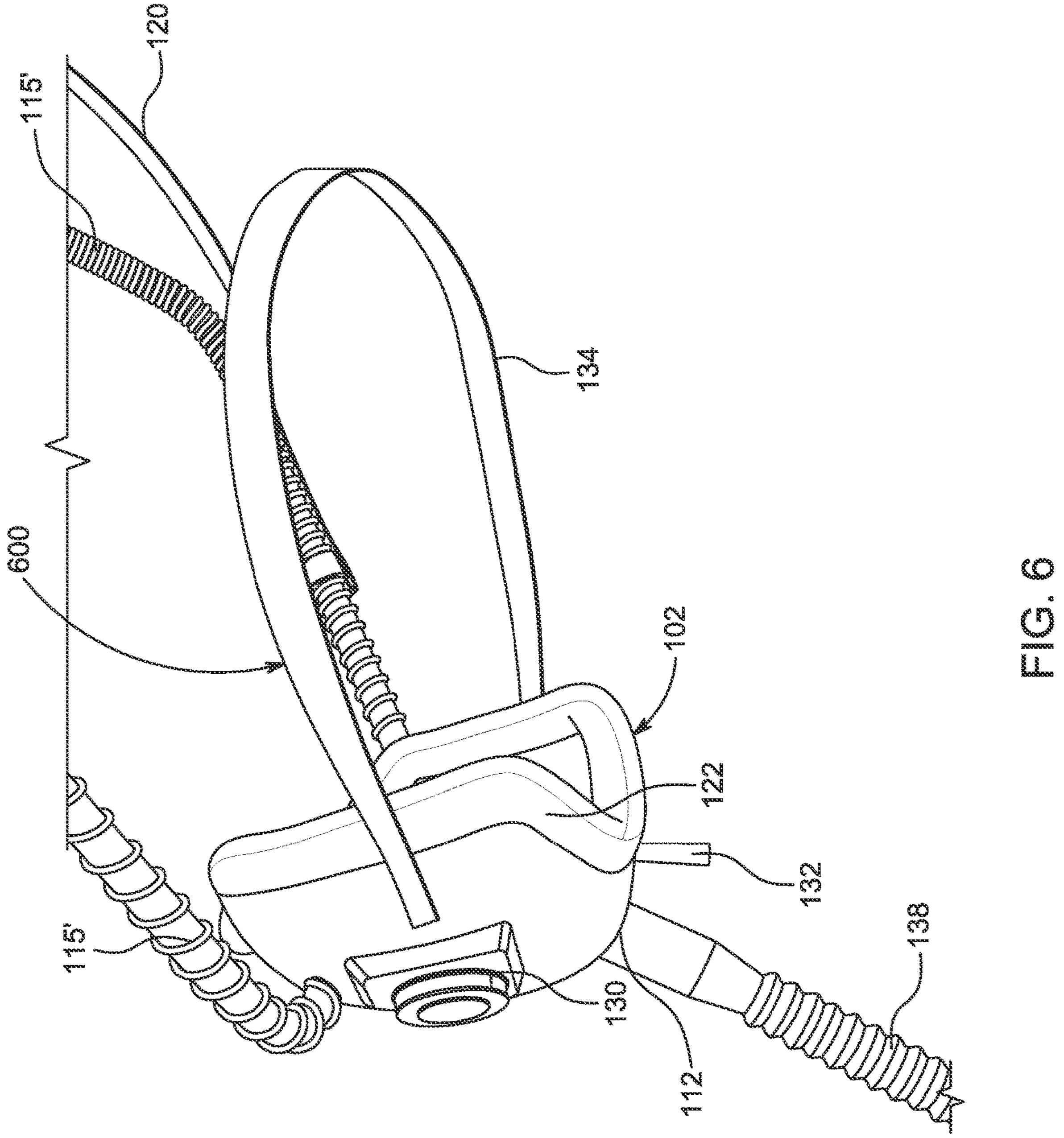
FIG. 6 shows a side view of the face mask of FIG. 3 including an inflatable peripheral seal, an inflatable valve and tube transition features that pass through the inlet ports defined on the mask body.

FIG. 6 shows a face mask 600, according to alternate preferred embodiments of the present arrangements. Face mask 600 includes mask body 102, exhaust port 112, adjustable head strap 120, peripheral seal 122, secondary airflow ports 130, inflatable valve 132 and retention strap 134, all of which are the same as those shown in connection with face mask 500 in FIG. 5. Further, face mask 600 includes tubes 115', which are the same as that shown in FIG. 3.

In certain embodiments of the present arrangements, a front portion of mask body 102, in face masks 100, 200, 300, 400, 500 and 600, is translucent or transparent to allow visibility into the interior side of mask body 102 and into at least two nasal prongs for facilitating adjustment of terminating ends (disposed on nasal prongs) into the nostrils of the subject.

The present teachings offer different methods for securing a face mask around a subject. One such exemplar method includes obtaining a mask body (e.g., mask body 102 shown in FIGS. 1-6) having disposed therein at least two nasal prongs (e.g., nasal prongs 108 shown in FIGS. 2 and 3), each of which terminates at a terminating end (e.g., terminating end 110 shown in FIGS. 2 and 3). Next, the exemplar method proceeds to positioning at least two of the terminating ends inside a subject's (e.g., a patient's) nostrils so that the terminating ends are positioned to effectively supply air flow and/or oxygen flow into the subject's nostrils. Then, the exemplar method includes wrapping one or more retention straps (e.g., retention strap 134 shown in FIGS. 3, 4, 5 and 6), which are attached to or part of the mask body, around a subject's head and securing the mask body to the subject's head such that the terminating ends continue to effectively provide air flow and/or oxygen flow into the subject's nostrils.

In those embodiments where the face mask of the present arrangements includes an inflatable peripheral seal 122 as shown in FIGS. 5 and 6, then the exemplar method for securing the face mask around the subject includes ensuring that a peripheral seal disposed around a circumference of the mask body snugly fits around subject's mouth and nose by activating an inflatable valve (e.g., inflatable valve 132 shown in FIGS. 5 and 6). In one embodiment of the present teachings, if peripheral seal 122 is not inflatable as shown in FIGS. 1 and 2, then this is accomplished by, preferably, applying a soft gel to the peripheral seal to effectively seal off the interior side of the mask body so that harmful toxins do not escape from the interior side of the mask body, without harming the subject's face particularly from prolonged application of the seal on the subject's face.

The exemplar method may be implemented when the face mask of the present arrangements is receiving air flow and/or oxygen flow into at least two of terminating ends from at least two tube transition features (e.g., tube transition features 106 of FIG. 2 or tube transition features 106' of FIG. 3), which are communicatively coupled to at least two tubes (e.g., tubes 115 of FIG. 2 or tubes 115' of FIG. 3), which are in turn communicatively coupled through a Y-split (e.g., Y-split 116 of FIG. 4) to a single tube e.g., single source tube 114 of FIG. 3), which in turn is communicatively coupled to an air supply source and/or an oxygen supply source. Under this scenario, the exemplar method includes ensuring placement of the Y-split behind a head of the subject so that air flow and/or oxygen flow to the subject's nostrils is unobstructed.

The exemplar method for securing the face mask around the subject also provide for adjusting nasal prongs to properly fit inside a subject's nostrils. To this end, the exemplar method includes holding or securing one or more tubes (e.g., tubes 115 of FIG. 2 or tubes 115' of FIG. 3, each of which convey air flow and/or oxygen flow to at least one tube transition feature (e.g., tube transition feature 106 of FIG. 2 or tube transition feature 106' of FIG. 3), which in turn conveys air flow and/or oxygen flow to the nasal prongs (e.g., nasal prongs 108 shown in FIGS. 2 and 3). Then the exemplar method includes guiding placement of the nasal prongs, contemporaneous with the above-mentioned step of holding or securing one or more tubes, into the nostrils of the subject, through the mask body. Guiding placement of the nasal prong through the mask body is facilitated by a flexible outer surface of the mask body or flexibility of the mask body at least around the mask body region that covers the subject's nostrils. As a result, a mask body that is made from a flexible material represents preferred embodiments of the present arrangements.

If necessary, the exemplar method also includes adjusting angular displacement of one or more of the tubes or one or more of the tube transition features about respective ones of the inlet ports (e.g., inlet ports 104 of FIGS. 1 and 2) to facilitate placement of the nasal prongs into the subject's nostrils. As explained above, either the tubes or the tube transition features pass through the inlet ports, which are defined on the mask body, to allow for their adjustment that impacts the positioning of nasal prongs inside the mask body and more specifically, inside the subject's nostrils.

In certain embodiments of the present arrangements, the inlet ports, through which tubes or the tube transition features pass, are defined on the mask body region that covers the subject's nostrils and are not defined on a side mask body region that is disposed on the sides of the mask body that cover the subject's cheeks or that is near the subject's jaw and away from the subject's nostrils. Defining inlet ports away from the mask body region that covers the subject's nostrils makes adjustment of the nasal prongs, inside the subject's nostrils, either difficult or impossible depending on the placement of the inlet ports.

In the present arrangements, the subject's exhaled air is, preferably, only removed through the exhaust port using, for example, the exhaust tube, and not removed through the nasal prongs.

Furthermore, the tubes (for conveying the air flow and/or oxygen flow) and the exhaust tube (for expelling the subject's exhaled air out of the mask body) do not travel in front of the subject's face to avoid accidental removal or yanking of the mask, and thereby interrupting air flow and/or oxygen flow into the subject's nostrils.

The present face mask arrangements, preferably, do not include a head strap and may be implemented neither as a full-face mask that substantially covers the subject's face, nor as a nasal only device, like a nasal cannula.

In preferred embodiments, the nasal prongs used in the present arrangements do not eliminate air and/or oxygen jetting. In fact, when the subject is sitting down and in an operational state of the present face mask, the nasal prongs will induce air and/or oxygen jetting as they are comfortably secured inside the subject's nostrils.

The face mask of the present arrangements, preferably, does not include valves or one or more filters for filtering air present inside a room and, preferably, is not a powered air purifying respirator for purifying air present inside a room.

In certain embodiments of the present arrangements, nasal prongs extend a length that ranges from about 10 mm to about 20 mm and a distance between two adjacent prongs inside a mask body ranges from about 12 mm to about 18 mm. A bridge feature may have a length that ranges from about 30 mm to about 35 mm. Tubes may have a length that ranges from about 320 mm to about 350 mm. The mask body may have a height (from the subject's chin to the top of the nose) that ranges from about 115 mm to about 155 mm, and may have a width (from mask body region covering one cheek to the adjacent cheek) that ranges from about 95 mm to about 120 mm.

The present teachings also provide many different methods for assembling a face mask. One such exemplar method begins with obtaining a mask body having defined therein, on or near a region that covers nostrils of a subject, at least two inlet ports that provide access between an exterior side of the mask and an interior side of the mask. The beginning of the exemplar method, preferably, includes obtaining at least two tubes that are communicatively coupled to or capable of being communicatively coupled to a source of air and/or a source of oxygen. The beginning of the exemplar step may also include obtaining at least two tube transition features that are integrated with or coupled to at least two nasal prongs.

The exemplar methods for assembling the face mask of the present arrangements then proceeds to passing, from the exterior side to the interior side, at least two of the tubes (e.g., tubes 115 of FIGS. 1 and 2) through at least two of the inlet ports (e.g., inlet ports 104 of FIGS. 1 and 2). Alternately, the exemplar method includes passing, from the interior side to the exterior side, at least two of the tube transition features (e.g., tube transition features 106' of FIG. 3) through at least two of the inlet ports (e.g., inlet ports 104 of FIGS. 1 and 2). Regardless of whether the tubes or the tube transition features pass through the inlet ports, the exemplar method includes coupling at least two of the tube transitioning features to at least two of the tubes to assemble the face mask of the present arrangements.

Exemplar methods for assembling may also include obtaining a mask body that also has defined therein an exhaust port. In these embodiments of the present teachings, the exemplar methods include communicatively coupling an exhaust tube to the exhaust port disposed on the mask body. The exhaust tube is coupled to a HEPA filter for filtering out harmful toxins from the subject's expelled exhaled air.

In preferred implementations of this exemplar method for assembling, the step of obtaining at least two tube transition features includes using a bridge feature. As a result, this step may begin with obtaining the bridge feature that includes at least two inlets and at least two of the tube transition features. The preferred implementations may then proceed to coupling at least two of the tubes with at least two of the inlets or coupling at least two of the tube transition features with at least two of the nasal prongs. It does not matter which coupling step is performed first so long as the tubes, tube transition features (of the bridge feature) and nasal prongs are connected to form at least a portion of the face mask of the present arrangements.

Although the invention is illustrated and described herein as embodied in one or more specific examples, it is nevertheless not intended to be limited to the details shown, since various modifications and structural changes may be made therein without departing from the spirit of the invention and within the scope and range of equivalents of the claims. Accordingly, it is appropriate that the appended claims be construed broadly, and in a manner consistent with the scope of the invention, as set forth in the following claims.

What is claimed is:

1. A face mask comprising:

a mask body including an interior side and an exterior side, said interior side configured to cover a mouth and a nose of a subject;

at least two inlet ports defined on an upper portion of a front of said mask body in a region that is configured to cover nostrils of said subject, said at least two inlet ports configured to provide access between said exterior side and said interior side of said mask body;

at least two tubes configured to convey air flow and/or oxygen flow and at least a portion of each of said at least two tubes is disposed on said exterior side of said mask body;

a bridge feature disposed in an interior of said mask body that structurally integrates at least two tube transition features that extend generally parallel to one another, each of which includes a portion that is disposed on said interior side of said mask body and is configured to advance air flow and/or oxygen flow received from a respective one of said at least two tubes towards said nostrils of said subject;

at least two nasal prongs extending from a connecting portion of said bridge feature, said connection portion configured to extend generally perpendicular to said at least two tube transition features and generally parallel to a face of said subject, each of said at least two nasal prongs communicatively coupled to at least one of said tube transition features and configured to further advance said air flow and/or oxygen flow towards or into said nostrils of said subject;

at least two terminating features, each of which is disposed around one of said nasal prongs and configured to occupy or stabilize said one of said nasal prongs within a nasal cavity inside one of said nostrils of said subject;

an exhaust tube, said exhaust tube connected to an exhaust port that is disposed on said mask body at a lower portion of said mask body in a region that is configured to be near said mouth of said subject;

at least two secondary air flow ports disposed on said mask body below said at least two inlet ports and above said exhaust port, each of said at least two secondary air flow ports comprising an embedded filtration element; and wherein said at least two tubes pass through said at least two inlet ports such that portions of said at least two tubes are present on said interior side of said mask body, or said at least two tube transition features pass through said at least two inlet ports such that portions of said at least two tube transition features are present on said exterior side of said mask body.

2. The face mask of claim 1, said exhaust port being configured to remove, out of said mask body, exhaled air present inside said interior of said mask body.

3. The face mask of claim 1, further comprising a single source tube extending to at least one Y-split that is configured for splitting air flow and/or oxygen flow inside said single source tube into said at least two tubes, and wherein said single source tube is communicatively coupled to a source of air and/or oxygen.

4. The face mask of claim 3, wherein said single source tube and/or said at least two tubes include smooth-bore tubing to facilitate high-flow oxygen and high-flow air delivery, and said face mask further comprising:

a circumferential clip disposed around each of said at least two tubes; and an adjustable head strap that couples at one end to one of said circumferential clips and is configured, at another end, to be disposed behind a head of the subject to stabilize positioning of said at least two tubes around the head of the subject.

5. The face mask of claim 4, wherein said single source tube and/or said at least two tubes are made from a corrugated material for facilitating efficient air flow and/or oxygen flow.

6. The face mask of claim 1, further comprising a peripheral seal disposed around a periphery of said mask body, wherein said peripheral seal includes a gel or is an inflatable portion configured for snugly fitting said mask body around the mouth and the nose of the subject.

7. The face mask of claim 1, wherein each terminating feature includes a first umbrella seal and a second umbrella seal, wherein said first umbrella seal includes a first base portion having a first diameter or a first dimension and said second umbrella seal includes a second base portion having a second diameter or a second dimension corresponding to said first dimension, wherein said first base portion is closer in distance than said second base portion to said connecting portion of said bridge feature, and wherein said first base portion has a greater diameter than the second base portion or said first dimension is larger than corresponding said second dimension, wherein said first and second dimensions are each measured across the respective base portions of said first and second umbrella seals.

8. The face mask of claim 1, wherein said at least two tubes pass through respective ones of said at least two inlet ports such that said portions of said at least two tubes are present on said interior side of said mask body, and wherein said at least two tubes are arranged to angularly displace about respective ones of said at least two inlet ports.

9. The face mask of claim 1, wherein said at least two tube transition features pass through respective ones of said at least two inlet ports such that said portions of said at least two tube transition features are present on the exterior side of said mask body, and wherein said at least two tube transition features are arranged to angularly displace about respective ones of said at least two inlet ports.

10. The face mask of claim 1, wherein at least a front portion of said mask body is transparent to allow visibility into said interior side of said mask body and of said at least two nasal prongs for facilitating adjustment into the nostrils of the subject.

11. The face mask of claim 1, wherein each embedded filtration element is configured to filter out at least 95% of airborne particles passing through its associated secondary airflow port.

12. The face mask of claim 2, further comprising a high-efficiency particulate air ("HEPA") filter coupled to said exhaust tube, which is connected to said exhaust port.

13. The face mask of claim 1, further comprising one or more mounting features for securing thereon retention straps configured to secure said mask body around the mouth and the nose of the subject.

* * * * *